United States Patent [19]

McGrath et al.

[11] Patent Number: 5,712,366
[45] Date of Patent: Jan. 27, 1998

[54] FABRICATION OF NANOSCALE MATERIALS USING SELF-ASSEMBLING PROTEINS

[75] Inventors: Kevin P. McGrath, Grafton; David L. Kaplan, Stow, both of Mass.

[73] Assignee: The United States of America as represented by the Secretary of the Army, Washington, D.C.

[21] Appl. No.: 452,592

[22] Filed: May 25, 1995

Related U.S. Application Data

[62] Division of Ser. No. 68,948, May 25, 1993, abandoned.

[51] Int. Cl.$^6$ .......................... A61K 38/00; C07K 5/00; C07K 7/00; C07K 16/00
[52] U.S. Cl. .............................................. 530/324
[58] Field of Search ................................. 530/324

[56] References Cited

U.S. PATENT DOCUMENTS

| | | | |
|---|---|---|---|
| 4,356,270 | 10/1982 | Itakura | 435/317 |
| 4,652,639 | 3/1987 | Stabinsky | 536/27 |
| 4,704,362 | 11/1987 | Itakura et al. | 435/253 |
| 4,748,119 | 5/1988 | Rich et al. | 435/172.3 |
| 4,888,286 | 12/1989 | Crea | 435/172.3 |
| 5,049,493 | 9/1991 | Khosla et al. | 435/69.1 |
| 5,096,815 | 3/1992 | Ladner et al. | 435/69.1 |
| 5,132,215 | 7/1992 | Jayaraman et al. | 435/91 |

OTHER PUBLICATIONS

McGrath et al., abstract entitled "Self-Assembling Nano-structures: Recognition and Ordered Assembly in Protein--Based Materials," publ. Nov. 1992, by Materials Research Society in regards to Biomolecular Materials Symposium.
McGrath and Kaplan, DARPA proposal entitled "Controlled Nanostructural Assembly," submitted May 4, 1992.
O'Shea et al., Science, vol. 243, pp. 538–542 (Jan 27, 1989).
O'Shea et al., Science, vol. 245, pp. 646–648 (Aug. 11, 1989).
Lupas et al., Science, vol. 252, pp. 1162–1164 (May 24, 1991).
O'Shea et al., Science, vol. 254, pp. 539–544 (Oct. 25, 1991).
O'Shea et al., X-Ray Structure of the GCN 4 Leucine zipper, a Two Stranded, Parallel Coiled Coil; Science (254) Oct. 1991 539–544.
O'Shea et al.: Preferential Heterodimer Formation by Isolated Leucine Zippers from Fos and Jun.; Science (245) Jun. 1989 646–648.
O'Shea et al.; Evidence That the Leucine Zipper is a Coiled Coil; Science (243) V89578–542.

*Primary Examiner*—Cecilia J. Tsang
*Assistant Examiner*—Jennifer Harle
*Attorney, Agent, or Firm*—John H. Lamming; Vincent J. Ranucci

[57] ABSTRACT

A method of fabricating nanoscale structural materials via the spontaneous organization of self-assembling proteins and the self-assembling proteins themselves. In a preferred embodiment of the invention, the self-assembling proteins included at least one occurrence of the following recognition sequence:

Ile Gly Asp Leu Xaa Asn Xaa Val Ala Gln Leu Xaa Arg Xaa Val Arg
1           5                    10                15

Ser Leu Xaa Asp Xaa Ala Ala Glu Leu Xaa Gln Xaa Val Ser Arg Leu
         20              25                  30

Xaa Asn Xaa Ile Glu Asp Leu Xaa Ala Xaa (SEQ ID NO:11)
       35                40 wherein Xaa is a charged residue selected from the group consisting of Glu, Lys, Arg and Asp, and the method comprises admixing proteins which include species of the aforementioned recognition sequence which are prone to dimerization, whereby the admixed proteins are caused to spontaneously organize into nanoscale structural materials via their respective recognition sequences.

3 Claims, 9 Drawing Sheets

|     | BstEII |     |         |     |         |
|-----|--------|-----|---------|-----|---------|
| 5'- GGT | GAC | CTG | [G/A]AA | AAC | [G/A]AA |
| Gly | Asp | Leu | Glu/Lys | Asn | Glu/Lys |

| GTG | GCC | CAG | CTG | [G/A]AA | AGG | [G/A]AA |
|-----|-----|-----|-----|---------|-----|---------|
| Val | Ala | Gln | Leu | Glu/Lys | Arg | Glu/Lys |

|     | BglII |     |     |         |     |         |
|-----|-------|-----|-----|---------|-----|---------|
| GTT | AGA | TCT | CTG | [G/A]AA | GAT | [G/A]AA |
| Val | Arg | Ser | Leu | Glu/Lys | Asp | Glu/Lys |

| GCG | GCT | GAA | CTG | [G/A]AA | CAA | [G/A]AA |
|-----|-----|-----|-----|---------|-----|---------|
| Ala | Ala | Glu | Leu | Glu/Lys | Gln | Glu/Lys |

|     | XhoI |     |     |         |     |         |
|-----|------|-----|-----|---------|-----|---------|
| GTC | TCG | AGA | CTG | [G/A]AA | AAT | [G/A]AA |
| Val | Ser | Arg | Leu | Glu/Lys | Asn | Glu/Lys |

| ATC | GAA | GAC | CTG | [G/A]AA | GCC | [G/A]AA |
|-----|-----|-----|-----|---------|-----|---------|
| Ile | Glu | Asp | Leu | Glu/Lys | Ala | Glu/Lys |

|     | BstEII |     |     |
|-----|--------|-----|-----|
| AAT | GGT | GAC | CTG -3' |
| Ile | Gly | Asp | Leu |

Fig. 1

```
          EcoRI          BstEII
5'- AATTC  GGT   GAC   CTG   [G/A]AA  AAC   [G/A]AA
3'- G      CCA   CTG   GAC   [C/T]TT  TTG   [C/T]TT
           Gly   Asp   Leu   Glu/Lys  Asn   Glu/Lys

GTC   GCC   CAG   CTG   [G/A]AA  AGG   [G/A]AA
    CAG   CGG   GTC   GAC   [C/T]TT  TCC   [C/T]TT
    Val   Ala   Gln   Leu   Glu/Lys  Arg   Glu/Lys

BglII        HindIII
    GTT   AGA   TCT   GA -3'
    CAA   TCT   AGA   CTTCGA -5'
    Val   Arg   Ser
```

Fig. 2A

```
          EcoRI        BglII
5'- AATTC  AGA   TCT   CTG   [G/A]AA  GAT   [G/A]AA
3'- G      TCT   AGA   GAC   [C/T]TT  CTA   [C/T]TT
           Arg   Ser   Leu   Glu/Lys  Asp   Glu/Lys

GCG   GCT   GAA   CTG   [G/A]AA  CAA   [G/A]AA
    CGC   CGA   CTT   GAC   [C/T]TT  GTT   [C/T]TT
    Ala   Ala   Glu   Leu   Glu/Lys  Gln   Glu/Lys

XhoI        HindIII
    GTC   TCG   AG    A -3'
    CAG   AGC   TC    TTCGA -5'
    Val   Ser   Arg
```

Fig. 2B

```
      EcoRI   XhoI
5'-   AATTC   TCG   AGA   CTG   [G/A]AA   AAT   [G/A]AA
  3'- G       AGC   TCT   GAC   [C/T]TT   TTA   [C/T]TT
              Ser   Arg   Leu   Glu/Lys   Asn   Glu/Lys

ATC   GAA   GAC   CTG   [G/A]AA   GCC   [G/A]AA
      TAG   CTT   CTG   GAC   [C/T]TT   CGG   [C/T]TT
      Ile   Glu   Asp   Leu   Glu/Lys   Ala   Glu/Lys

BstEII          HindIII
      AAT   GGT   GAC   C        A -3'
      TTA   CCA   CTG   G        TTCGA -5'
      Ile   Gly   Asp   Leu
```

Fig. 2C

```
     XbaI        BamHI             NheI          BstEII
5'-CTAGA    GGA TCC   ATG   GCT   AGC   GGT   GAC   CTG
      T    CCT AGG   TAC   CGA   TCG   CCA   CTG   GAC
                     Gly Ser   Met   Ala   Ser   Gly   Asp   Leu

SpeI           BamHI      XbaI
AAT   AAC   ACT   AGT   GGG ATC C   T -3'
TTA   TTG   TGA   TCA   CCC TAG G   AGATC -5'
Asn   Asn   Thr   Ser   Gly   Ile
```

Fig. 3

Ile Gly Asp Leu Glu Asn Glu Val Ala Gln Leu Glu Arg Glu Val Arg
1           5                    10                   15

Ser Leu Glu Asp Glu Ala Ala Glu Leu Glu Gln Lys Val Ser Arg Leu
            20                   25                   30

Lys Asn Glu Ile Glu Asp Leu Lys Ala Glu Ile Gly Asp Leu Glu Asn
            35                   40                   45

Glu Val Ala Gln Leu Glu Arg Glu Val Arg Ser Leu Glu Asp Glu Ala
            50                   55                   60

Ala Glu Leu Glu Gln Lys Val Ser Arg Leu Lys Asn Glu Ile Glu Asp
65                   70                   75                   80

Leu Lys Ala Glu

Fig. 4A

Ile Gly Asp Leu Lys Asn Lys Val Ala Gln Leu Lys Arg Lys Val Arg
1           5                    10                   15

Ser Leu Lys Asp Lys Ala Ala Glu Leu Lys Gln Glu Val Ser Arg Leu
            20                   25                   30

Glu Asn Glu Ile Glu Asp Leu Lys Ala Lys Ile Gly Asp Leu Lys Asn
            35                   40                   45

Lys Val Ala Gln Leu Lys Arg Lys Val Arg Ser Leu Lys Asp Lys Ala
            50                   55                   60

Ala Glu Leu Lys Gln Glu Val Ser Arg Leu Glu Asn Glu Ile Glu Asp
65                   70                   75                   80

Leu Lys Ala Lys

Fig. 4B

Ile Gly Asp Leu Lys Asn Lys Val Ala Gln Leu Glu Arg Glu Val Arg
1            5                   10                  15

Ser Leu Lys Asp Lys Ala Ala Glu Leu Lys Gln Glu Val Ser Arg Leu
            20                  25                  30

Glu Asn Glu Ile Glu Asp Leu Lys Ala Lys Ile Gly Asp Leu Lys Asn
            35                  40                  45

Lys Val Ala Gln Leu Glu Arg Glu Val Arg Ser Leu Lys Asp Lys Ala
     50                  55                  60

Ala Glu Leu Lys Gln Glu Val Ser Arg Leu Glu Asn Glu Ile Glu Asp
65             70                  75                  80

Leu Lys Ala Lys

Fig. 4C

Ile Gly Asp Leu Glu Asn Glu Val Ala Gln Leu Glu Arg Glu Val Arg
1            5                   10                  15

Ser Leu Lys Asp Lys Ala Ala Glu Leu Lys Gln Glu Val Ser Arg Leu
            20                  25                  30

Glu Asn Glu Ile Glu Asp Leu Lys Ala Lys Ile Gly Asp Leu Glu Asn
            35                  40                  45

Glu Val Ala Gln Leu Glu Arg Glu Val Arg Ser Leu Lys Asp Lys Ala
     50                  55                  60

Ala Glu Leu Lys Gln Glu Val Ser Arg Leu Glu Asn Glu Ile Glu Asp
65             70                  75                  80

Leu Lys Ala Lys

Fig. 4D

Ile Gly Asp Leu Glu Asn Glu Val Ala Gln Leu Glu Arg Glu Val Arg
1 5 10 15

Ser Leu Glu Asp Glu Ala Ala Glu Leu Lys Gln Glu Val Ser Arg Leu
20 25 30

Glu Asn Glu Ile Glu Asp Leu Lys Ala Lys Ile Gly Asp Leu Glu Asn
35 40 45

Glu Val Ala Gln Leu Glu Arg Glu Val Arg Ser Leu Glu Asp Glu Ala
50 55 60

Ala Glu Leu Lys Gln Glu Val Ser Arg Leu Glu Asn Glu Ile Glu Asp
65 70 75 80

Leu Lys Ala Lys

Fig. 4E

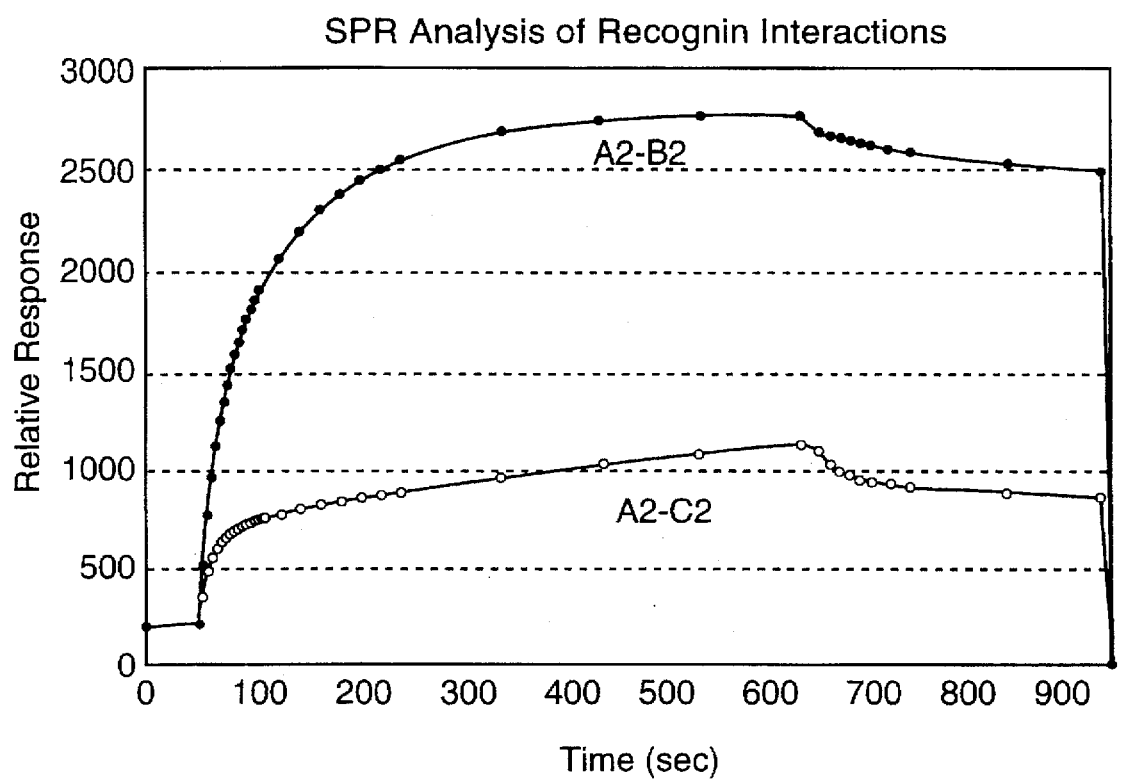
Fig. 5  Surface plasmon resonance measurements of the interactions between A2-B2 and A2-C2 at 25μg/mL concentration of A2.

FABRICATION OF NANOSCALE MATERIALS USING SELF-ASSEMBLING PROTEINS

RELATED APPLICATION

This is a division of patent application Ser. No. 08/068,948, filed May 25, 1993, now abandoned.

STATEMENT OF U.S. GOVERNMENT INTEREST

The invention described herein may be manufactured, used and licensed by or for the Government for Governmental purposes without the payment to us of any royalty thereon.

BACKGROUND OF THE INVENTION

The present invention relates both to a method of fabricating nanoscale materials using self-assembling proteins and to the self-assembling proteins used to fabricate such nanoscale materials.

Without some form of recognition process, controlled assembly at the molecular scale is not feasible. The incorporation of such recognition into polymeric systems cannot be accomplished without exacting control over residue sequence and functionality. Conventional methods for incorporating more than one monomer into polymers are limited by (1) statistical control over the sequence distribution and (2) a disparity in molecular weight. Additionally, the range of functional groups that can be incorporated is severly limited by the type of polymerization method used. Only by exploiting the virtually error-free synthetic machinery of biological systems can one produce materials capable of both recognition and self-assembly into functional nanoscale devices and structural components.

Efficient engineering at the molecular scale relies on two things: (1) the ability of individual molecules to recognize specific counterparts in multicomponent systems; and (2) the spontaneous organization of hundreds or thousands of molecules into well-defined molecular complexes. In traditional materials science, the level of such organization rarely extends down to the molecular level. The ordering of individual molecules is statistical in nature, and often considerable post-assembly processing is required to achieve the desired physical properties. In contrast, nanometer scale fabrication techniques rely on the molecules to process themselves into useful assemblies. This can only be accomplished by incorporating into each component the ability to spontaneously recognize where it belongs within a larger framework and to rapidly incorporate into the final, desired product.

The importance of recognition processes in nature cannot be overemphasized. These interactions form the basis for virtually every biological process in living organisms. Nature has developed a large array of specific recognition patterns, based on shape, hydrophobicity, charge placement, and allosteric interactions. Understanding of these recognition patterns has progressed rapidly in the past few years, particularly in the specificity of interaction seen in transcriptional regulatory proteins.

Patents and publications of interest to the present invention include the following, all of which are incorporated herein by reference: O'Shea et al., "Evidence That the Leucine Zipper Is a Coiled Coil," *Science*, Vol. 243, pp. 538–542 (Jan. 27, 1989); O'Shea et al., "Preferential Heterodimer Formation by Isolated Leucine Zippers from Fos and Jun," *Science*, Vol. 245, pp. 646–648 (Aug. 11, 1989); O'Shea et al., "X-ray Structure of the GCN4 Leucine Zipper, a Two-Stranded, Parallel Coiled Coil, *Science*, Vol. 254, pp. 539–544 (Oct. 25, 1991); Lupas et al., *Science*, Vol. 252, pp. 1162–1164 (May 24, 1991); PCT application No. WO 92/09695 published Jun. 11, 1992; and U.S. Pat. No. 5,026,815, inventors Ladner et al., issued Mar. 17, 1992.

SUMMARY OF THE INVENTION

The present invention is directed to a new and novel method for fabricating nanoscale structural materials. According to the teachings of the present invention, said method of fabrication involves the use of artificial polypeptides (i.e. non-naturally-occurring amino acid sequences) specifically designed as building blocks and containing features of molecular recognition which permit the spontaneous self-assembly thereof when mixed together. Because they are capable of spontaneously self-assembly, the polypeptides can be used to form novel materials designed for specific functions, including membranes, fibers, absorbants, reactive materials, etc. Preferably, the subject polypeptides are incorporated into natural or recombinant proteins via synthetic gene constructs. The recombinant materials may then be produced in microorganism, purified from the fermentation, and assembled. Alternatively, these proteins may also be produced using synthetic peptide chemistry.

According to one aspect of the invention, the structure, sequence, size, composition and stereochemistry of the self-assembling polypeptides can be precisely controlled using genetic processes.

According to another aspect of the invention, the extent and degree of side-to-side recognition between different polypeptides can be manipulated by the placement of charged monomers and hydrophobic monomers within the polypeptide sequence.

According to still another aspect of the invention, the extent and degree of end-to-end recognition between polypeptide sequences can be manipulated by the selection of desired functional end groups at the ends of the polypeptide sequences.

According to still yet another aspect of the invention, specific linkers may be incorporated into or added onto said polypeptide sequences to control multimerization.

One application of the above-described technology is in the fabrication of improved designs of selectively permeable membranes for protective gloves and coated fabrics for fuel handlers and other hazardous materials. This is because the present technology permits one to precisely tailor pore sizes and pore reactivity, to control the hydrophobic/hydrophilic nature of pore lining, and to add responsive elements (e.g., enzymes, antibodies, light receptors) into pores in such a way as to permit one to design a desired barrier from the molecular level up.

Another application of the above-described technology is in the formation of fibers having precisely controlled structures and functions. Since such fibers can be assembled from the molecular scale to the macroscopic scale, ultimate alignments/orientation and maximal tensile properties should be achievable. In addition, with the selective incorporation of mineral-building domains, ceramic composites can be designed for specific impact-resistant armor applications.

Still another application of the above-described technology is in the fabrication of selective filtration systems.

Still yet another application of the above-described technology is in the fabrication of materials for controlled release of pharmaceuticals or other chemicals or microorganisms. Materials for medical implants, wound healants and other medical treatments would also be feasible using this technology.

Additional objects, features, aspects, advantages and applications of the present invention will be set forth in part in the description which follows, and in part will be obvious from the description or may be learned by practice of the invention. The objects, features, aspects, advantages and applications of the present invention may be realized and attained by means of the instrumentalities and combinations particularly pointed out in the appended claims.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In these drawings:

FIG. 1 represents a DNA sequence (SEQ ID NO: 1) which may be used to encode an entire library of recognition sequences;

FIGS. 2A (SEQ ID NO:2), 2B (SEQ ID NO:3) and 2C (SEQ ID NO:4) represent three DNA fragments used to construct the DNA sequence of FIG. 1 (SEQ ID NO:1);

FIG. 3 (SEQ ID NO:5) represents the DNA linker sequence used to insert the sequence of FIG. 1 (SEQ ID NO:1) into pUC18;

FIGS. 4A (SEQ ID NO:6), 4B (SEQ ID NO:7), 4C (SEQ ID NO:8), 4D (SEQ ID NO:9) and 4E (SEQ ID NO:10) represent five different amino acid sequences which may be obtained using the DNA sequence of FIG. 1 (SEQ ID NO:1);

FIG. 5 is a graphic representation of the surface plasmon resonance measurements of the interactions between the respective amino acid sequences of FIG. 4A (SEQ ID NO:6) and FIG. 4B (SEQ ID NO:7) and between the respective amino acid sequences of FIG. 4A (SEQ ID NO:6) and FIG. 4C (SEQ ID NO:8)

DETAILED DESCRIPTION OF PREFERRED EMBODIMENTS

Figure 6A:
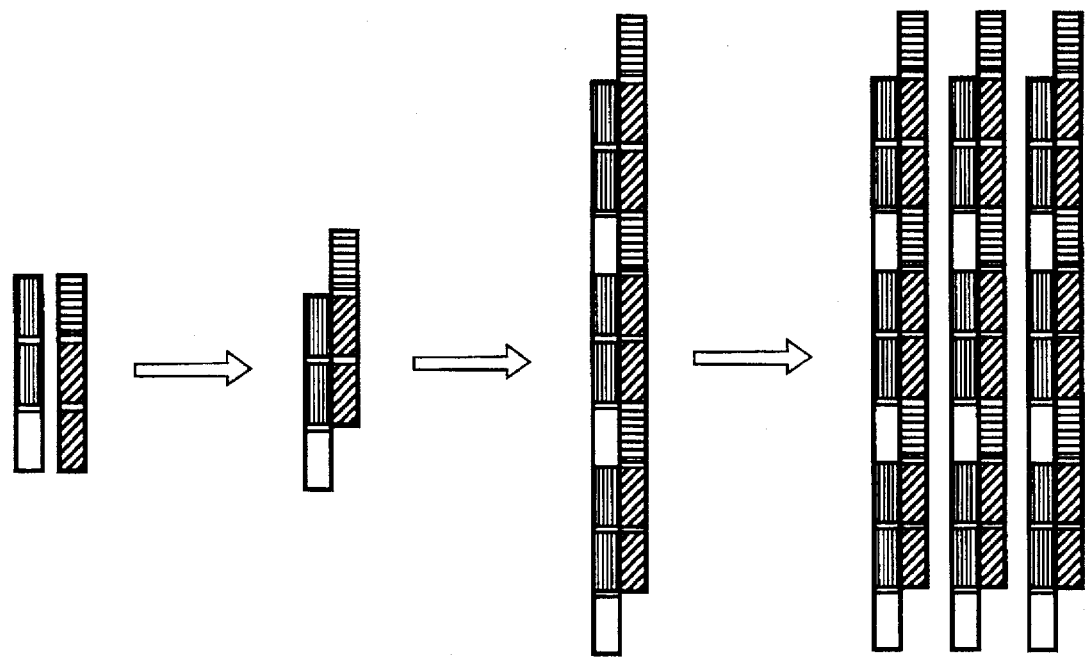
FIGS. 6A and 6B are schematic depictions of exemplary applications to which the amino acid sequences of the present invention may be put.

As noted above, the present invention relates to the design and construction of self-assembling protein-based structural materials, the formation of which is mediated by "recognition sequences" which are incorporated into individual components of the ordered macroscopic structure and which drive the spontaneous self-organization thereof. The "recognition elements," which are in fact non-naturally occurring amino acid sequences, control the molecular organization and assembly of the materials into which they are incorporated, and can be combined in different patterns and proportions to generate complex molecular architectures and functions. The interactions described herein most frequently occur between two or more different amino acid sequences to construct ordered hierarchical structures but need not be limited thereto. Typically, these amino acid sequences range in size from as small as 14 residues to as large as 100 residues.

Amino acid sequences capable of functioning as recognition sequences preferably contain either only one type of structure (e.g., alpha helix, beta sheet, beta turn) or multiple elements in well-defined orders and proportions (e.g., antibody combining sites or antigenic epitopes).

Initial sequences chosen have focused on coiled-coil alpha helices as the defined secondary structure within the recognition motifs. Amino acid sequences were optimized for coiled-coil formation, and were designed to mimic natural "leucine zipper" protein sequences known to mediate specific dimerization in many transcriptional regulatory proteins. The introduction of specificity into such structures is accomplished by controlling the identity and placement of charged residues on the faces of each helix.

The degree of organization in coiled coils, at the secondary, tertiary and quarternary levels, makes them ideal candidates for primary components in self-assembling systems. Unique to these materials is the precise spatial control, over hundreds of angstroms, of functional group placement. Additionally, the high degree of specificity exhibited in the dimerization of such transcriptional regulatory proteins as Fos and Jun can be incorporated into novel synthetic proteins, producing material capable of spontaneous self-organization into complex supramolecular assemblies. However, it should be stressed that the present invention is broad enough in scope to encompass other types of interacting structures, including but not limited to, beta sheets, helix-loop-helix structures, and single chain antibody-antigen interactions.

As noted above, initial focus was placed on controlling molecular scale assembly through coiled coil dimerization. Considerations which were used to formulate specific recognition sequences included the following: (1) placing a hydrophobic leucine every seventh residue to aid in the formation of coiled-coil alpha helices; (2) placing charged residues at specific locations to create electrostatic recognition patterns; (3) eliminating sequences prone to homodimerize; and (4) using sequences which would control solubility in the dimeric state. (As can readily be appreciated, sequences can also be designed to specifically homodimerize, if desired.)

With these considerations in mind, the following set of amino acid sequences was formulated:

(SEQ ID NO:11)
Ile Gly Asp Leu Xaa Asn Xaa Val Ala Gln Leu Xaa Arg Xaa Val Arg
1                5                    10                   15
Ser Leu Xaa Asp Xaa Ala Ala Glu Leu Xaa Gln Xaa Val Ser Arg Leu
       20                    25                       30
Xaa Asn Xaa Ile Glu Asp Leu Xaa Ala Xaa
       35                 40 wherein Xaa is a charged residue selected from the group consisting of Glu and Lys. (It should be noted that other charged residues, such as Arg and Asp, may also be used instead of or in combination with Glu and Lys.)

If the above polypeptide sequence is viewed as a series of heptad subunits (a-b-c-d-e-f-g), leucine can be thought of as being positioned at the d position, and charged residues, such as glutamic acid and lysine, can be thought of as being positioned at the e and g positions. Electrostatic bonding is believed to occur between the e residue of the ith heptad and the g residue of the ith-1 heptad. As can readily be appreciated, the number of possible charge patterns for this sequence is extremely large and forms the foundation for a library of sequences that can be mixed or matched in patterns that define the type and degree of self-organization.

One should be able to predict in advance the affinity between any two or more sequences of the set by constructing sequences whose charge patterns vary in a defined manner and by then testing their respective affinities for other sequences of defined charge patterns.

It should also be understood that the above-described amino acid sequence could be repeated, in its entirety, any number of times to give polypeptides of varying lengths.

Referring now to FIG. 1, there is shown a DNA sequence (SEQ ID NO:1) obtained by reverse translation which may be used to encode the entire library of recognition sequences for the polypeptide sequence shown above (SEQ ID NO:11). Codons were chosen to maximize the expression level in *E. coli* and to introduce useful restriction sites for subsequent genetic manipulation. The length and composition of the amino acid sequence was chosen not only to create sophisticated recognition motifs, but also to minimize the repetitive nature of the corresponding gene. The DNA sequences use a "mixed site" approach at the first base of the codons for amino acids at the e and g positions. An [A/G] mixed site synthesis is used to generate either AAA (Lys) or GAA (Glu) codons at these positions. Thus, in a single step, a library of DNA sequences encoding all possible recognition sequences can be generated.

The DNA sequence of FIG. 1 (SEQ ID NO:1) was constructed from three sets of smaller synthetic DNA fragments that can be combined to encode the entire 42 amino acid sequence. These sequences were designed with EcoRI and HindIII termini to facilitate cloning and sequencing of each fragment in pUC18. The sequences of these three smaller fragments are presented in FIGS. 2A (SEQ ID NO:2), 2B (SEQ ID NO:3) and 2C (SEQ ID NO:4), respectively.

After insertion into pUC18 and verification of individual fragments by double stranded plasmid sequencing, a library of each fragment set was generated. The individual fragments were excised from the recombinant pUC18 by digestion with either BstEII and BglII, BglII and XhoI or XhoI and BstEII (depending on the fragment sequence). These smaller fragments were then combined into a single large fragment having two BstEII termini, which encoded one of the thousands of different protein sequences described earlier.

The BstEII-ended DNA fragments were then inserted into a recombinant pUC18 containing the linker sequence shown in FIG. 3 (SEQ ID NO:5) inserted into the XbaI site. DNA fragments were inserted into the BstEII site of the recombinant vector, and the ligation mix was used to transform *E. coli* NM522. Properly constructed genetic elements were verified by the sequencing of plasmids demonstrating restriction digestion patterns consistent with the presence of insert.

As noted previously, the variations in charge identity and placement on individual helices create specific binding domains for dimerization. Only helices with complementary charge patterns will typically be energetically favored for dimerization. The five amino acid sequences shown in FIGS. 4A (SEQ ID NO:6), 4B (SEQ ID NO:7), 4C (SEQ ID NO:8), 4D (SEQ ID NO:9) and 4E (SEQ ID NO:10), respectively, have been manufactured in accordance with the teachings of the present invention. Because Lys and Glu are oppositely charged, one would expect that, based on electrostatic considerations, the polypeptide of FIG. 4A (SEQ ID NO:6— also referred to herein as polypeptide A2) would be more likely to dimerize with the polypeptide of FIG. 4B (SEQ ID NO:7—also referred to herein as polypeptide B2) than with the polypeptide of FIG. 4C (SEQ ID NO:8—also referred to herein as polypeptide C2) or, least of all, with itself. These expectations appear to have been confirmed by the experiments described below.

First, the interaction between polypeptides A2 and B2 was investigated using turbidity measurements at 400 nm. The proteins were believed to exist as weak homodimers in solution; upon mixing, however, the more stable heterodimer was formed. When the polypeptides were mixed at equal concentrations, a rapid increase in turbidity was seen. This was attributed to specific heterodimer formation, which subsequently associated into higher order structures that precipitated in solution. Gel analysis of the precipitate indicated that it was a 1:1 complex of polypeptides A2 and B2. No similar increase in the turbidity of the homodimer solutions was observed prior to mixing.

Next, the interaction of polypeptide A2 with polypeptides B2 and C2, when both of the components were free in solution and when one species was immobilized onto a gold film, was examined. The immobilization tests were performed to measure the rates of association and dissociation between the complexes. Surface plasmon resonance was used to detect minute changes in refractive index that accompanied a specific binding event in the immediate vicinity of the metal surface. The results of these surface plasmon resonance measurements are shown in FIG. 5. As can be seen therein, there is a measurable difference in both the rates and magnitude of interaction between polypeptides A2 and B2 as compared to that between polypeptides A2 and C2. After an initial increase in refractive index due to solvent exchange, it is seen that the rate of association for the A2-B2 complex was more rapid and that the equilibrium response was achieved sooner. There does not seem to be a great difference in the rates of dissociation (seen in the later portions of the sensorgram). A kinetic anaylsis of these rate constants run at several different concentrations of A2 reveals that for the A2-B2 interaction, $k_{ass}=4.11\times10^3$, $k_{diss}=1.31\times10^{-3}$, and $K_a=3.14\times10^6$. For the A2-C2 interaction, $k_{ass}=3.46\times10^3$, $k_{diss}=2.39\times10^3$, and $K_a=1.45\times10^6$.

Figure 6B:
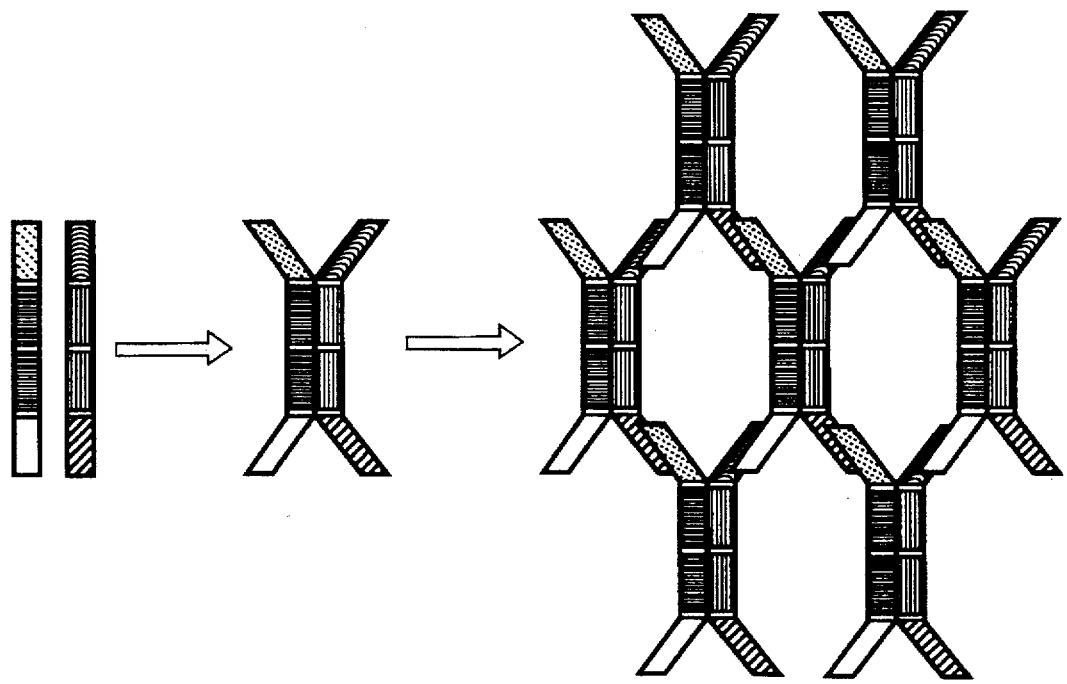

As can readily be appreciated, the polypeptides of the present invention can be used to fabricate complex self-assembling materials. Examples of such materials are shown in FIGS. 6A and 6B. In the first instance (FIG. 6A), that of the self-assembling fibers, the genes for polypeptides A2 and B2 are modified by incorporating additional recognition elements at the N- or C- termini. These new elements, which are designed to react with each other and not with polypeptides A2 or B2, impose a new driving force for ordered supramolecular assembly, and align all of the dimers in a "head-to-tail" orientation within a growing fibril. Such fibers should have excellent mechanical properties, along with unique piezo- and pyroelectric activity.

The second example (FIG. 6B), that of an ordered network formation, is a logical extension of ordered fiber assembly. In this instance, the fiber-forming genes are further modified to introduce a third set of recognition sites that will control growth and organization in three dimensions. Such materials will have highly uniform and controlled pore sizes that could be exploited in optics, thermal insulation, selectively permeable membranes, controlled release, or medical reconstruction.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of fabricating a self-assembling protein-based structural material comprising the steps of:
    a) providing a multiplicity of a first artificial polypeptide sequence having a coiled-coil alpha helical secondary structure comprised of a first peptide series having at least two heptad subunits characterized by the generic formula (a-b-c-d-e-f-g) wherein d is Leu and e and g are charged residues;
    b) providing a multiplicity of a second artificial polypeptide sequence having a coiled-coil alpha helical secondary structure comprised of a second peptide series having at least two heptad subunits characterized by the generic formula (a-b-c-d-e-f-g) wherein d is Leu and e and g are charged residues, said second artificial polypeptide sequence being different from said first artificial polypeptide sequence and being designed to spontaneously heterodimerize with said first artificial polypeptide sequence when admixed therewith;
wherein said first and second artificial polypeptide sequences are synthesized by a recombinant process comprising the steps of:
    i) obtaining a DNA sequence by reverse translation;
    ii) using a mixed site synthetic approach to generate either a Lys or Glu codon at the e and g positions of each heptad;
    iii) constructing the DNA sequence from smaller synthetic DNA fragments; and
    iv) inserting the DNA sequence thus constructed into a host vector;
    v) expressing the first and second polypeptide sequences by the host cells; and
    vi) isolating the first and second polypeptide sequences thus expressed by chemical separation means;
    c) admixing said multiplicities of said first and second artificial polypeptide sequences, whereby said first and said second artificial polypeptide sequences spontaneously heterodimerize into a self-assembled protein-based structural material.

2. The method as claimed in claim 1 wherein each of said first artificial polypeptide sequence and said second artificial polypeptide sequence comprises a species of the following generic sequence:

(SEQ ID NO:11)
```
Ile Gly Asp Leu Xaa Asn Xaa Val Ala Gln Leu Xaa Arg Xaa Val Arg
 1               5                  10                  15
Ser Leu Xaa Asp Xaa Ala Ala Glu Leu Xaa Gln Xaa Val Ser Arg Leu
            20                  25                  30
Xaa Asn Xaa Ile Glu Asp Leu Xaa Ala Xaa
        35              40
``` wherein Xaa is a charged residue selected from the group consisting of Glu, Lys, Arg and Asp.

3. The method as claimed in claim 2 wherein Xaa is a charged residue selected from the group consisting of Glu and Lys.

* * * * *

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
    ( A ) LENGTH: 135 base pairs
    ( B ) TYPE: nucleic acid
    ( C ) STRANDEDNESS: double
    ( D ) TOPOLOGY: linear ( x i ) SEQUENCE DESCRIPTION: SEQ ID NO: 1:

```
GGT  GAC  CTG  RAA  AAC  RAA  GTG  GCC  CAG  CTG  RAA  AGG  RAA  GTT   42
Gly  Asp  Leu  Xaa  Asn  Xaa  Val  Ala  Gln  Leu  Xaa  Arg  Xaa  Val
1                        5                        10

AGA  TCT  CTG  RAA  GAT  RAA  GCG  GCT  GAA  CTG  RAA  CAA  RAA  GTC   84
Arg  Ser  Leu  Xaa  Asp  Xaa  Ala  Ala  Glu  Leu  Xaa  Gln  Xaa  Val
15                       20                       25

TCG  AGA  CTG  RAA  AAT  RAA  ATC  GAA  GAC  CTG  RAA  GCC  RAA  AAT  126
Ser  Arg  Leu  Xaa  Asn  Xaa  Ile  Glu  Asp  Leu  Xaa  Ala  Xaa  Ile
     30                      35                       40

GGT  GAC  CTG                                                         135
Gly  Asp  Leu
          45
```

( 2 ) INFORMATION FOR SEQ ID NO: 2:

( i ) SEQUENCE CHARACTERISTICS:
    ( A ) LENGTH: 55 base pairs
    ( B ) TYPE: nucleic acid
    ( C ) STRANDEDNESS: double
    ( D ) TOPOLOGY: linear ( x i ) SEQUENCE DESCRIPTION: SEQ ID NO: 2:

```
AATTC  GCT  GAC  CTG  RAA  AAC  RAA  GTG  GCC  CAG  CTG  RAA  AGG  RAA 44
       Gly  Asp  Leu  Xaa  Asn  Xaa  Val  Ala  Gln  Leu  Xaa  Arg  Xaa
       1                        5                        10

GTT  AGA  TCT  GA                                                      55
Val  Arg  Ser
     15
```

( 2 ) INFORMATION FOR SEQ ID NO: 3:

( i ) SEQUENCE CHARACTERISTICS:
    ( A ) LENGTH: 53 base pairs
    ( B ) TYPE: nucleic acid
    ( C ) STRANDEDNESS: double
    ( D ) TOPOLOGY: linear ( x i ) SEQUENCE DESCRIPTION: SEQ IS NO: 3:

```
AATTC  AGA  TCT  CTG  RAA  GAT  RAA  GCG  GCT  GAA  CTG  RAA  CAA  RAA
       Arg  Ser  Leu  Xaa  Asp  Xaa  Ala  Ala  Glu  Leu  Xaa  Gln  Xaa
       1                   5                        10

GTC  TCG  AGA
Val  Ser  Arg
          15
```

( 2 ) INFORMATION FOR SEQ ID NO: 4:

( i ) SEQUENCE CHARACTERISTICS:
    ( A ) LENGTH: 55 base pairs
    ( B ) TYPE: nucleic acid
    ( C ) STRANDEDNESS: double
    ( D ) TOPOLOGY: linear ( x i ) SEQUENCE DESCRIPTION: SEQ ID NO: 4:

| AATTC | TCG | AGA | CTG | RAA | AAT | RAA | ATC | GAA | GAC | CTG | RAA | GCC | RAA | 44 |
|---|---|---|---|---|---|---|---|---|---|---|---|---|---|---|
| | Ser | Arg | Leu | Xaa | Asn | Xaa | Ile | Glu | Asp | Leu | Xaa | Ala | Xaa | |
| | 1 | | | | 5 | | | | | 10 | | | | |

| AAT | GGT | GAC | CA | 55 |
|---|---|---|---|---|
| Ile | Gly | Asp | | |
| | 15 | | | |

( 2 ) INFORMATION FOR SEQ ID NO: 5:

( i ) SEQUENCE CHARACTERISTICS:
        ( A ) LENGTH: 49 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 5:

| CTAGA | GGA | TCC | ATG | GCT | AGC | GGT | GAC | CTG | AAT | AAC | ACT | AGT | 41 |
|---|---|---|---|---|---|---|---|---|---|---|---|---|---|
| | Gly | Ser | Met | Ala | Ser | Gly | Asp | Leu | Asn | Asn | Thr | Ser | |
| | 1 | | | | 5 | | | | | 10 | | | |

| GGG | ATC | C | T | 49 |
|---|---|---|---|---|
| Gly | Ile | | | |

( 2 ) INFORMATION FOR SEQ ID NO: 6:

( i ) SEQUENCE CHARACTERISTICS:
        ( A ) LENGTH: 84 amino acids
        ( B ) TYPE: amino acid
        ( D ) TOPOLOGY: linear ( x i ) SEQUENCE DESCRIPTION: SEQ ID NO: 6:

| Ile | Gly | Asp | Leu | Glu | Asn | Glu | Val | Ala | Gln | Leu | Glu | Arg | Glu | Val | Arg |
|---|---|---|---|---|---|---|---|---|---|---|---|---|---|---|---|
| 1 | | | | 5 | | | | | 10 | | | | | 15 | |

| Ser | Leu | Glu | Asp | Glu | Ala | Ala | Glu | Leu | Glu | Gln | Lys | Val | Ser | Arg | Leu |
|---|---|---|---|---|---|---|---|---|---|---|---|---|---|---|---|
| | | | 20 | | | | | 25 | | | | | 30 | | |

| Lys | Asn | Glu | Ile | Glu | Asp | Leu | Lys | Ala | Glu | Ile | Gly | Asp | Leu | Glu | Asn |
|---|---|---|---|---|---|---|---|---|---|---|---|---|---|---|---|
| | | | 35 | | | | 40 | | | | | 45 | | | |

| Glu | Val | Ala | Gln | Leu | Glu | Arg | Glu | Val | Arg | Ser | Leu | Glu | Asp | Glu | Ala |
|---|---|---|---|---|---|---|---|---|---|---|---|---|---|---|---|
| | 50 | | | | | 55 | | | | | 60 | | | | |

| Ala | Glu | Leu | Glu | Gln | Lys | Val | Ser | Arg | Leu | Lys | Asn | Glu | Ile | Glu | Asp |
|---|---|---|---|---|---|---|---|---|---|---|---|---|---|---|---|
| 65 | | | | | 70 | | | | | 75 | | | | | |

| Leu | Lys | Ala | Glu |
|---|---|---|---|

( 2 ) INFORMATION FOR SEQ ID NO: 7:

( i ) SEQUENCE CHARACTERISTICS:
        ( A ) LENGTH: 84 amino acids
        ( B ) TYPE: amino acid
        ( D ) TOPOLOGY: linear ( x i ) SEQUENCE DESCRIPTION: SEQ ID NO: 7:

| Ile | Gly | Asp | Leu | Lys | Asn | Lys | Val | Ala | Gln | Leu | Lys | Arg | Lys | Val | Arg |
|---|---|---|---|---|---|---|---|---|---|---|---|---|---|---|---|
| 1 | | | | 5 | | | | | 10 | | | | | 15 | |

| Ser | Leu | Lys | Asp | Lys | Ala | Ala | Glu | Leu | Lys | Gln | Glu | Val | Ser | Arg | Leu |
|---|---|---|---|---|---|---|---|---|---|---|---|---|---|---|---|
| | | | 20 | | | | | 25 | | | | | 30 | | |

| Glu | Asn | Glu | Ile | Glu | Asp | Leu | Lys | Ala | Lys | Ile | Gly | Asp | Leu | Lys | Asn |
|---|---|---|---|---|---|---|---|---|---|---|---|---|---|---|---|
| | | | 35 | | | | 40 | | | | | 45 | | | |

| Lys | Val | Ala | Gln | Leu | Lys | Arg | Lys | Val | Arg | Ser | Leu | Lys | Asp | Lys | Ala |
|---|---|---|---|---|---|---|---|---|---|---|---|---|---|---|---|
| | 50 | | | | | 55 | | | | | 60 | | | | |

| Ala | Glu | Leu | Lys | Gln | Glu | Val | Ser | Arg | Leu | Glu | Asn | Glu | Ile | Glu | Asp |
|---|---|---|---|---|---|---|---|---|---|---|---|---|---|---|---|
| 65 | | | | | 70 | | | | | 75 | | | | | 80 |

Leu Lys Ala Lys ( 2 ) INFORMATION FOR SEQ ID NO: 8:

( i ) SEQUENCE CHARACTERISTICS:
        ( A ) LENGTH: 84 amino acids
        ( B ) TYPE: amino acid
        ( D ) TOPOLOGY: linear ( x i ) SEQUENCE DESCRIPTION: SEQ ID NO: 8:

```
Ile Gly Asp Leu Lys Asn Lys Val Ala Gln Leu Glu Arg Glu Val Arg
1               5                   10                  15

Ser Leu Lys Asp Lys Ala Ala Glu Leu Lys Gln Glu Val Ser Arg Leu
            20                  25                  30

Glu Asn Glu Ile Glu Asp Leu Lys Ala Lys Ile Gly Asp Leu Lys Asn
            35                  40                  45

Lys Val Ala Gln Leu Glu Arg Glu Val Arg Ser Leu Lys Asp Lys Ala
    50                  55                  60

Ala Glu Leu Lys Gln Glu Val Ser Arg Leu Glu Asn Glu Ile Glu Asp
65                  70                  75                  80

Leu Lys Ala Lys
```

( 2 ) INFORMATION FOR SEQ ID NO: 9:

( i ) SEQUENCE CHARACTERISTICS:
        ( A ) LENGTH: 84 amino acids
        ( B ) TYPE: amino acid
        ( D ) TOPOLOGY: linear ( x i ) SEQUENCE DESCRIPTION: SEQ ID NO: 9:

```
Ile Gly Asp Leu Glu Asn Glu Val Ala Gln Leu Glu Arg Glu Val Arg
1               5                   10                  15

Ser Leu Lys Asp Lys Ala Ala Glu Leu Lys Gln Glu Val Ser Arg Leu
            20                  25                  30

Glu Asn Glu Ile Glu Asp Leu Lys Ala Lys Ile Gly Asp Leu Glu Asn
            35                  40                  45

Glu Val Ala Gln Leu Glu Arg Glu Val Arg Ser Leu Lys Asp Lys Ala
    50                  55                  60

Ala Glu Leu Lys Gln Glu Val Ser Arg Leu Glu Asn Glu Ile Glu Asp
65                  70                  75                  80

Leu Lys Ala Lys
```

( 2 ) INFORMATION FOR SEQ ID NO: 10:

( i ) SEQUENCE CHARACTERISTICS:
        ( A ) LENGTH: 84 amino acids
        ( B ) TYPE: amino acid
        ( D ) TOPOLOGY: linear ( x i ) SEQUENCE DESCRIPTION: SEQ ID NO: 10:

```
Ile Gly Asp Leu Glu Asn Glu Val Ala Gln Leu Glu Arg Glu Val Arg
1               5                   10                  15

Ser Leu Glu Asp Glu Ala Ala Glu Leu Lys Gln Glu Val Ser Arg Leu
            20                  25                  30

Glu Asn Glu Ile Glu Asp Leu Lys Ala Lys Ile Gly Asp Leu Glu Asn
            35                  40                  45

Glu Val Ala Gln Leu Glu Arg Glu Val Arg Ser Leu Glu Asp Glu Ala
    50                  55                  60

Ala Glu Leu Lys Gln Glu Val Ser Arg Leu Glu Asn Glu Ile Glu Asp
```

-continued

```
                65                       70                     75                          80
            Leu Lys Ala Lys
```

( 2 ) INFORMATION FOR SEQ ID NO: 11:

( i ) SEQUENCE CHARACTERISTICS:
        ( A ) LENGTH: 42 amino acids
        ( B ) TYPE: amino acid
        ( D ) TOPOLOGY: linear ( x i ) SEQUENCE DESCRIPTION: SEQ ID NO: 11:

```
Ile Gly Asp Leu Xaa Asn Xaa Val Ala Gln Leu Xaa Arg Xaa Val Arg
 1               5                  10                  15

Ser Leu Xaa Asp Xaa Ala Ala Glu Leu Xaa Gln Xaa Val Ser Arg Leu
            20                  25                  30

Xaa Asn Xaa Ile Glu Asp Leu Xaa Ala Xaa
        35              40
```